(12) United States Patent
Lewis et al.

(10) Patent No.: US 7,189,562 B2
(45) Date of Patent: *Mar. 13, 2007

(54) MONONUCLEAR PHAGOCYTES IN THERAPEUTIC DRUG DELIVERY

(75) Inventors: Claire E. Lewis, Sheffield (GB); Adrian L. Harris, Oxford (GB); Julian M Marshall, Oxford (GB)

(73) Assignee: Oxford BioMedica (UK) Limited, Oxford (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 197 days.

(21) Appl. No.: 09/284,009

(22) PCT Filed: Oct. 8, 1997

(86) PCT No.: PCT/GB97/02709

§ 371 (c)(1),
(2), (4) Date: Apr. 5, 1999

(87) PCT Pub. No.: WO98/15294

PCT Pub. Date: Apr. 16, 1998

(65) Prior Publication Data

US 2002/0061294 A1 May 23, 2002

(30) Foreign Application Priority Data

| Oct. 9, 1996 | (GB) | 9620952 |
| Jan. 30, 1997 | (GB) | 9701975 |
| Feb. 21, 1997 | (GB) | 9703670 |

(51) Int. Cl.
*C12N 15/85* (2006.01)

(52) U.S. Cl. .............. 435/325; 435/320.1; 435/455
(58) Field of Classification Search ........... 435/325, 435/320.1, 455, 240.1, 69.1; 424/450, 9, 424/321; 514/44, 2
See application file for complete search history.

(56) References Cited

U.S. PATENT DOCUMENTS

| 5,942,434 A | * | 8/1999 | Ratcliffe et al. | 435/320.1 |
| 5,972,900 A | * | 10/1999 | Ferkol et al. | 514/44 |
| 6,265,390 B1 | | 7/2001 | Ratcliffe | |
| 6,379,647 B2 | | 4/2002 | Lewis | |

FOREIGN PATENT DOCUMENTS

| WO | WO 95/06120 | 3/1995 |
| WO | WO 95/21927 | 8/1995 |
| WO | WO 95/29074 | 11/1995 |

OTHER PUBLICATIONS

J. Gomez–Navarro et al. Gene Therapy of Cancer Jun. 1999, Eur. J. Cancer 35 (6): 867–885.*
Verma et al. Nature, vol. 389, 1997, pp. 239–242.*
Orkin et al. Report and Recommendations of the Panel to Assess the NIH Investment in Research on Gene Therapy, www.nih.gov.*
Kaufmann et al Xenotransplantation. 1995. Annu Rev Immunol vol 13 pp 339–367.*
Crystal Transfer of genes to humans early lessons and obstacles to success, 1995. Science, vol. 270, pp. 404–410.*
Nishihara et al, Endocrinology, vol. 138, No. 11 ()1997) pp 45774583.
Kluth et al, The Journal of Immunology, 2001, 166: 4728–4736 (2001).
Ferkol et al, "Receptor–Mediated Gene Transfer into Macrophages", *Proceedings of the National Academy of Sciences*, U.S.A., vol. 93, Jan. 1996, pp. 101–105.
Database Medline Abstract 97077027, Erbacher et al, "Gene Transfer by DNA/Glycosylated Polylysine Complexes into Human Blood Monocyte–Derived Macrophages", *Human Gene Therapy*, vol. 7, No. 6. Apr. 10, 1996, pp. 721–729.
Database Medline Abstract 95239217, Kim et al, "High Dose Methylprednisone Therapy Reduces Expression of JE/MCP–1 MRNA and Macrophage Accumulation in the Ischemic Rate Brain". *Journal of the Neurological Sciences*, vol. 128, No. 1, Jan. 1995, pp. 28–35.
Knighton et al, "Oxygen tension Regulates the Expression of Angiogenes Factor by Macrophages", *Science*, vol. 221, 1983, pp. 1283–1285.
Vukanovic et al, "Linomide Inhibits Angiogenesis, Growth. Matastasis, and Macrophage Infiltration within Rage Prostatic Cancers", *Cancer Research*, vol. 55, 1995, pp. 1499–1504.
Leek et al, "Association of Macrophage Infiltration with Angiogenesis and Prognosis in Invasive Breast Carcinoma". *Cancer Research*, vol. 56. Oct. 15, 1996. pp. 4625–4629.
Lewis et al, "Role of Macrophages in Tumour Angiogenesis: Regulation by Hypoxia". *Pathological Society of Great Britain and Ireland*, 175 Meeting, vol. 182, Jul. 2–4, 1997, Sheffield, p. 1A.

* cited by examiner

*Primary Examiner*—Dave Trong Nguyen
*Assistant Examiner*—Celine Qian
(74) *Attorney, Agent, or Firm*—Townsend and Townsend and Crew LLP (57) ABSTRACT

The invention relates to the exploitation of the migratory behavior of mononuclear phagocytes with a view to targeting therapeutic drug delivery. The invention therefore concerns the attachment or incorporation of a therapeutic agent to or into a mononuclear phagocyte and the subsequent migration of the munonuclear phagocyte to a target area.

20 Claims, 8 Drawing Sheets

Top panel

Bottom panel

MONONUCLEAR PHAGOCYTES IN THERAPEUTIC DRUG DELIVERY

The invention relates to a method of drug delivery; means therefor including components thereof which have particular, but not exclusive, application in cancer therapy development.

Macrophages often comprise 20–60% of the tumour cell mass in breast carcinomas and form intimate contacts with malignant cells. This has long been thought to represent part of the host's defence mechanisms against the tumour; however, their function at such sites in the body remains an enigma at present as macrophages isolated from human or murine tumours exhibit reduced tumouricidal and antigen-presenting activities compared to those from normal tissues (1).

Monocytes are produced in the bloodstream and extravasate (i.e. exit) into surrounding tissues including such diseased tissues as malignant tumours and atherosclerotic plaques, where they differentiate into macrophages and perform immune, secretory, phagocytic and other functions. Monocytes and macrophages are collectively termed mononuclear phagocytes. As tissue macrophages have a lifespan of 60 to 90 days and the number of macrophages in tumours remains constant, it is believed that there is a constant attachment of monocytes to the tumour endothelium and influx of monocytes into the tumour cell mass.

Hypoxia, that is, very low levels of oxygen, exist only in some forms of diseased tissue (e.g. malignant tumours, ischaemic heart tissue etc). Hypoxia and/or hypoglycaemia is thought to occur in growing tumours when the increasing metabolic demands of the rapidly expanding tumour cell population outstrip the supply of oxygen/glucose etc., made available to them by simple diffusion across the tumour mass from vessels in surrounding normal tissues.

Ischaemia, that is, a deficiency of blood flow to part of the body also exists in some forms of diseased tissue (e.g. malignant tumours, ischaemic heart tissue etc). Malignant tumours tend to outgrow their blood supply and often have ischaemic areas of tumour cell apoptosis and necrosis. Moreover, the vascular supply in some tumour areas can collapse resulting in the formation of further ischaemic areas. Ischaemic tissues are also found in coronary artery disease, diabetic retinopathy and following strokes. Cells in such areas of vascular occlusion or collapse experience various forms of stress such as glucose deprivation, low pH, elevated levels of lactate and pyruvate, ion or c natic imbalance and hypoxia.

Figure 1:
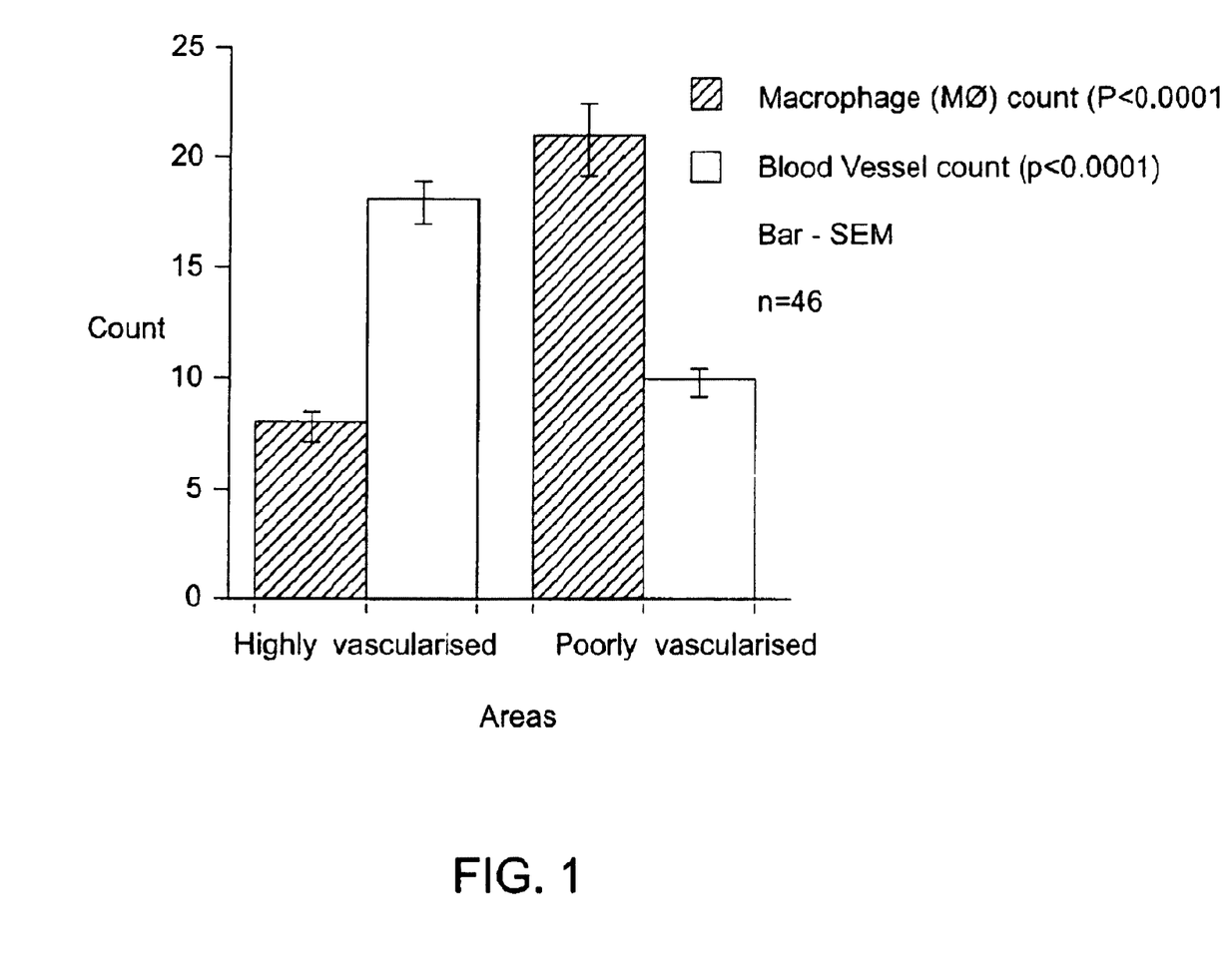
FIG. 1 shows the distribution of macrophages in areas of high and low vascularity in 46 invasive breast carcinomas (i.e. assessed by quantification of CD31 postivity of blood vessels; see reference 3).
Figure 2:
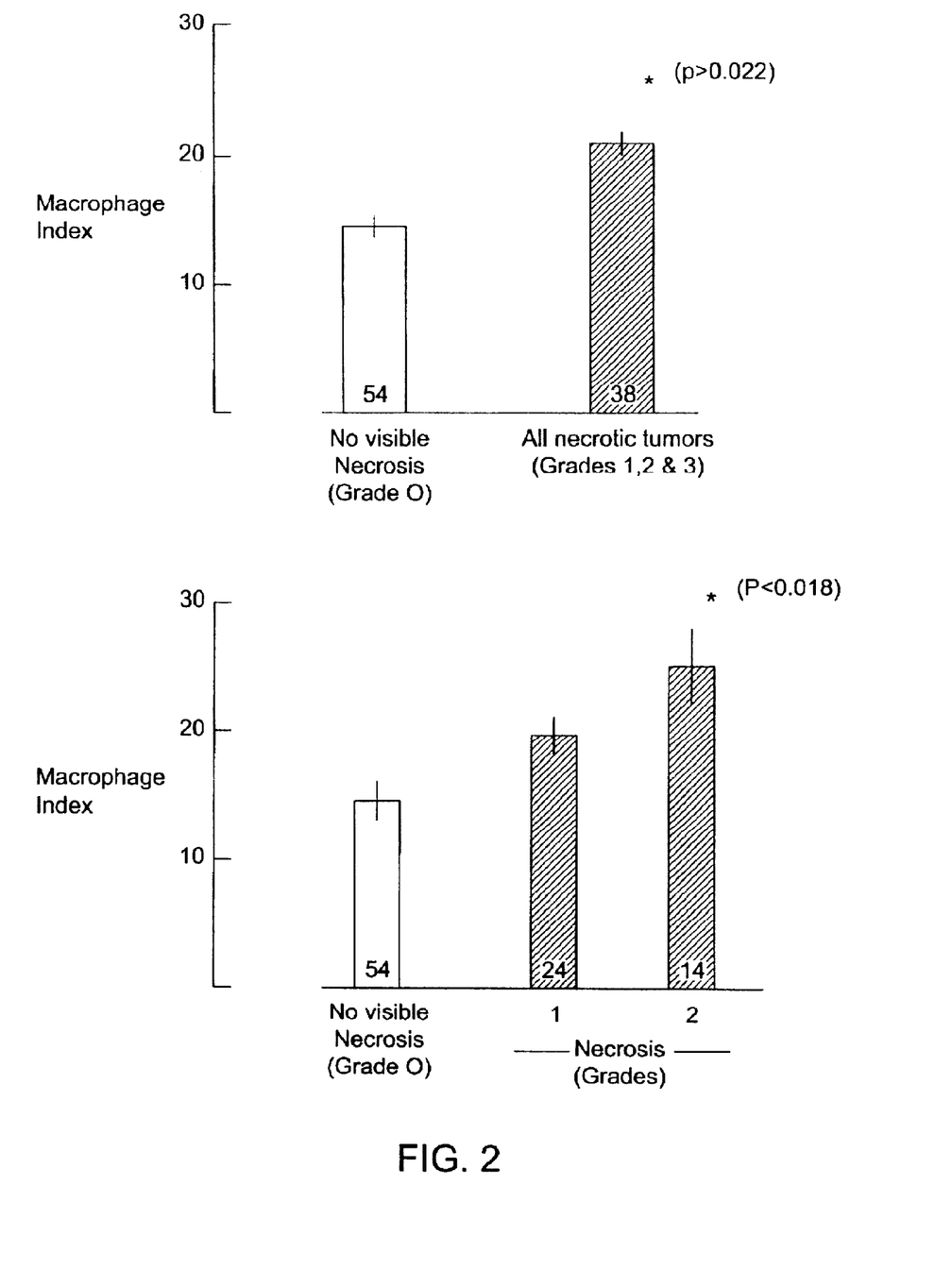
FIG. 2 shows association of macrophage index with necrosis in 92 breast carcinomas. * w.r.t Grade O group (Mann Whitney U Test). Number of data points in each group is indicated at the base of each column. [Grades for necrosis: 0, no necrosis; 1, few focal areas of necrosis; 2, many focal areas of necrosis; 3, almost entirely necrotic].

Our recent and surprising data indicate that once monocytes enter a tumour from the bloodstream and differentiate into macrophages, they preferentially congregate in hypoxic (i.e. poorly vascularised and necrotic) sites deep within a tumour mass remote from blood vessels (2). Refer to FIG. 1, which represents a bar chart of the Distribution of Macrophages in Relation to Blood Vessels. Moreover, breast tumours, with more hypoxic/necrotic areas, are more heavily infiltrated with macrophages, which preferentially locate to, or around, the necrotic sites (refer to FIG. 2, which represents a bar chart of the Association of Macrophage Index with Necrosis in Breast Carcinomas). Very recently, macrophages have also been shown to congregate in ischaemic/necrotic sites in ovarian tumours (3). Over a decade ago experimental hypoxia was shown to induce the production of angiogenic factors by macrophages in vitro (2). Taken together these data could underpin our recent finding, that increased numbers of macrophages in breast tumours equate with higher levels of angiogenesis and increased fatalities in breast cancer (2).

We examined tumour biopsies from 100 breast cancer patients, and found that macrophage infiltration was strongly associated with reduced relapse-free interval and overall survival—even in lymph node negative patients alone (i.e. the better prognosis group). Indeed macrophage infiltration proved to be almost as important in predicting outcome as lymph node status in breast cancer. We went on to see if this was due to an effect of macrophages on such important parameters of tumour aggressiveness as the mitotic index, receptor status, degree of angiogenesis, etc. It was at this point that a highly significant and unexpected correlation between the degree of macrophage infiltration within a tumour mass and angiogenesis emerged, suggesting a role for this cell type in some or all of the steps of tumour angiogenesis (2).

Our unique observations suggest that, since the entry or presence of macrophages into or in such diseased tissues appears to be deleterious to the patient, therapies specifically focused on either blocking their entry; their destruction; and/or their exploitation to carry therapeutic agents into such diseased tissues could prove to have therapeutic benefits.

Monoclonal antibodies have been considered for many years to be the best way of delivering cytotoxic agents to tumours, but this approach has so far been disappointing in clinical trials (4, 5). The main reason for the lack of therapeutic efficacy of antibody conjugates in solid tumours is the resistance of the turnour to penetration by macromolecules. In studies with radiolabelled antibodies, typically only 0.001–0.01% of the injected dose localises to each gram of solid tumours in humans (6, 7). The poor penetration of antibodies is thought to be due to a number of factors. Firstly, the antibodies must cross the physical barrier of the endothelial cell layer in tumour blood vessels and the, often dense, fibrous stroma packed between tumour cell areas. Secondly, the dense packing of tumour cells and tight junctions between epithelial tumour cells hinder the transport of the antibody within the tumour mass. Thirdly, the absence of lymphatics within the tumour contributes to the build up of a high interstitial pressure which opposes the influx of molecules into the tumour core.

One solution to the poor penetration of antibody conjugates into solid tumours would be to attack the endothelial cells in the tumour, instead of the tumour cell themselves, which are readily accessible to intravenously injected antibody. This then leads to destruction of the tumour blood vessels and the death of neighbouring tumour cells which rely on the blood supply for oxygen and nutrients. Early studies using murine models have met with some success in this area (8), but there remains the problem in humans of how to target tumour endothelial cells and not those in normal tissues. Furthermore, as mentioned earlier, our work strongly suggests the tumour necrosis resulting from this approach will trigger compensatory angiogenic activities in tumour-infiltrating macrophages in the vicinity. This would oppose the effects of the therapeutic agent.

Our inventive solution is to attach the agent (e.g. tumour or endothelial cell cytotoxin) to monocytes in the peripheral blood, that is the cells which gain entry to the tumour in large numbers to form tumour-infiltrating macrophages. Since monocytes swarm to the tumour site in large numbers as an early and ongoing event in tumour development, they can be used to carry therapeutic agents (e.g. cytotoxic drugs or toxins) into the centre of solid tumours. In support of this suggestion is the fact that many studies have shown that malignant tumours actively recruit this cell type and that monocytes then follow a chemotactic trail produced by tumour cells. Further, we have uniquely shown that mononuclear phagocytes congregate in tumour areas where they are most needed, i.e. hypoxic or stress areas, possibly to help initiate angiogenesis.

Although we have described the invention with particular reference to tumour cells, it can be used in any instance where mononuclear phagocytes infiltrate or are attracted to hypoxic/ischaemic/stress tissue or conditions. Thus, the invention can be used during development to control the vascularisation of developing tissue, typically, but not exclusively, with a view to targeting a hypoxia regulatable agent so as to promote or enhance vascularisation. Alternatively the invention can be used to target hypoxia regulatable agents to damaged tissue, for example to tissue where de-vascularisation has occurred following damage to the vascular system via an amputation, stroke, cardiac arrest, extreme hypertension, ischaemia, burns etc.

It follows from the information provided herein that the invention may be used to prevent or reduce tissue vascularisation, or to promote or enhance vascularisation, or to simply deliver selected drugs to hypoxic/ischaemic/stress sites where mononuclear phagocytes are typically present.

In addition, given our finding that mononuclear phagocytes infiltrate or are attracted to hypoxic/ischaemic/stress tissue or conditions the invention can also be used with a view to targeting a stress regulatable agent such as an ischaemically regulatable agent. Thus, in the instance where mononuclear phagocytes infiltrate a site which is also ischaemic and thus characterised by glucose deprivation, low pH, elevated levels of lactate or pyruvate, and/or hypoxia it is possible to arrange for targeting of an ischaemically regulatable agent.

It is therefore an object of the invention to provide a novel drug delivery system which exploits the fact that mononuclear phagocytes collect or are attracted to hypoxic or ischaemic or stress sites.

It is yet a further object of the invention to provide a regulatable drug delivery system which enables the activation of said drug to be controlled, and more specifically, to be controlled so as to only be active under hypoxic and/or stress and/or ischaemic conditions.

It is yet a further object of the invention to provide a novel drug for use in the drug delivery system of the invention.

The invention, in its broadest aspect, comprises the use of mononuclear phagocytes to deliver therapeutic agents to tissues and especially hypoxic and/or stress and/or ischaemic sites.

According to a first aspect of the invention there is therefore provided a therapeutic composition comprising a regulatable agent and an agent that binds to a cell surface element of a mononuclear phagocyte.

In a preferred embodiment of the invention said binding agent preferentially binds to said cell surface element.

Reference herein to the term preferentially is intended to include the selective or targeted binding of said agent to mononuclear phagocytes.

In a preferred embodiment said agent is a hypoxia and/or ischaemia and/or stress regulatable agent.

It will therefore be apparent that the hypoxia and/or ischaemia and/or stress regulatable agent will be affected by hypoxic and/or ischaemic and/or stress conditions and typically affected so as to only be active in such conditions. Moreover, said binding agent, which is typically coupled to said regulatable agent, attaches the composition to mononuclear phagocytes and so targets the regulatable agent, to sites typically infiltrated by mononuclear phagocytes. Thus in the instance where said mononuclear phagocytes penetrate hypoxic and/or ischaemic and/or stress sites said composition is suitably delivered to such sites and the regulatable agent becomes active.

The invention is elegant in so far as the body's own mechanisms are exploited for the specific delivery of drugs but the invention is safe in so far as the drugs remain inactive until exposed to hypoxic and/or ischaemic and/or stress conditions.

Given the above nature of the invention agents suitable for use in manufacturing the said composition will be known to those skilled in the art and therefore the following preferred embodiments are not intended to be exhaustive but rather illustrative.

For example, in one embodiment of the invention said hypoxia regulatable agent may comprise a therapeutic gene, that is to say a nucleotide sequence encoding a therapeutic agent which is under the control of a hypoxia sensitive agent such as a hypoxia regulated expression element i.e. a promoter or enhancer which is sensitive to hypoxia. Thus, under conditions of hypoxia said element will be activated so as to enable the gene encoding the therapeutic agent to be expressed. In this embodiment of the invention the binding agent comprises an agent that ensures internalisation of said therapeutic gene, for example, without limitation a viral or a non-viral vector, with a view to incorporating same into the mononuclear phagocyte genome.

In addition, or alternatively, the hypoxia regulatable therapeutic gene may encode a prodrug activation enzyme, that is to say an enzyme which converts a relatively inactive drug into a more active one. An example of this kind of enzyme is thymidine phosphorylase which activates the 5-FU prodrugs capcetabine and furtulon. Another example of a prodrug activation enzyme is the herpes simplex thymidine kinase or cytosine deaminase which, once internalised into the mononuclear phagocytes would act as a reservoir for activation of the prodrugs ganciclovir and 5-fluorocytosine.

Another example of a prodrug activation enzyme is the P450 family e.g. CyP2B6 which activate cyclofosfamide and ifosfamide (30)

Other examples of hypoxia regulatable therapeutic genes are to be found in PCT/GB95/00322 (WO9521927).

Alternatively said hypoxia regulatable agent may comprise a bioreductively activated drug prodrug such as RSU1069 or Tirapazamine which are activated at very low levels of oxygen as well as with contact with enzymes such as reductases. Thus, where not only hypoxia, but protein action, typically enzymic, is required for activation of said regulatable agent, said therapeutic composition of the invention may further comprise an agent that activates said hypoxia regulatable agent, such as a reductase and/or a gene encoding said reductase.

In a further embodiment of the invention said ischaemia or stress regulatable agent may comprise a therapeutic gene, that is a gene encoding a therapeutic agent which is under the control of an ischaemia or stress sensitive agent such as an ischaemia or stress regulated expression element i.e. a promoter or enhancer which is sensitive to any one or more of the factors characterising ischaemia or stress such as, for example, without limitation, glucose deprivation, low pH, elevated levels of lactate or pyruvate and/or ion or osmotic imbalance. Thus, under conditions of ischaemia or stress said elements will be activated so as to enable the gene encoding the therapeutic agent to be expressed. In this embodiment of the invention the binding agent comprises an agent that ensures internalisation of said therapeutic gene with a view to incorporating same into the mononuclear phagocyte genome.

As mentioned above, the ischaemia or stress regulatable agent may comprise a pro-drug activation enzyme as previously described, or a gene encoding same.

Suitable examples of DNA sequences known to be activated by any of the aforementioned factors, or "stress factors" may be used in the invention and examples of such sequences include, without limitation, promoter and/or enhancer sequences activated by glucose deprivation, low pH or elevated levels of lactate or pyruvate and/or ion or osmotic imbalance. For example, the glucose-regulated proteins (grp's) such as grp78 and grp94 are highly conserved proteins known to be induced by glucose deprivation (19). The grp78 gene is expressed at low levels in most normal healthy tissues under the influence of basal level promoter elements, but has at least two critical "stress-inducible regulatory elements" upstream of the TATA element (19, 20). Attachment to a truncated, 632-base pair sequence of the 5' end of the grp78 promoter (which include these two stress-inducible regulatory sacs) confers high inducibility to glucose deprivation on reporter genes in vitro (20). Furthermore, use of this promoter sequence in a retroviral vector drove high level expression of a reporter gene in tumour cells in murine fibrosarcomas, particularly in central, relatively ischaemic/necrotic sites (20). In addition it is thought that grp78 may be inducible by other stress factors (27).

Another group of highly conserved, what may be termed, "stress proteins" are those responsive to low pH. The genes for these proteins are known to have acid-inducible promoters, examples of which have been cloned and characterised in recent studies (21) indeed, it was demonstrated that the acid-inducibility of several such defined DNA sequences in hybrid DNA constructs consisting of each one of these fused to a reporter gene encoding a green fluorescent protein was sensitive to pH. Maximum induction was seen when the pH was dropped to 4.5.

Thus, said stress regulatable agent comprises a therapeutic gene under the control of a stress regulated expression element known to those skilled in the art. Notably, a stress regulated expression element is intended to include both homologous and heterologous elements i.e. that is to say promoters and/or enhancers for genes known to be expressed, or over-expressed, by mononuclear phagocytes in stress conditions; and promoters or enhancers for genes known to be over-expressed by other tissues in said conditions, respectively. Examples of the former group include the expression element of the osteopontin gene and thymidine phosphorylase gene. Other examples of homologous promoters or enhancers comprise those involved in the phagocytic activity of macrophages including CD36, CD68, thrombospondin, the αvβ3 integin and low density lipoprotein receptors (25, 26).

In a yet alternative embodiment of the invention said agent may be regulated by means other than hypoxia or ischaemia or stress.

Indeed, the use of hypoxia or ischaemia or stress to regulate the expression/activity of a therapeutic gene may not be an exclusive feature of the utilisation of mononuclear phagocytes as a means of targeting therapeutic genes to tumours or regions of hypoxia/ischaemia/stress.

In a further embodiment of the invention it may be preferable to place the therapeutic gene under the control of an inducible or repressible promoter element, transcription from which can be modulated to regulate the effective dose of the therapeutic gene. This may result in more accurate control of expression of the therapeutic gene and thereby reduce undesirable side effects as a consequence of the gene therapy.

By way of example, a constitutively active promoter used to express a therapeutic gene/agent is placed under the regulation of the antibiotic tetracycline by inclusion in the promoter of the tetracycline repressor DNA sequence. The vector DNA incorporating the therapeutic promoter cassette includes the DNA sequence of the tetracycline repressor protein under the control of a suitable promoter element. Transfection of said DNA construct into the mononuclear phagocyte genome results in expression of tetracycline repressor protein and a repression in the transcription of the therapeutic gene. Transfected mononuclear phagocytes are then re-introduced into a patient to allow said phagocyte to infiltrate, for example, a tumour. Tetracycline is then administered orally, via an intravenous route, or injected directly into the tumour tissue. The administration of tetracylcine to the patient results in inactivation of the binding between the tetracycline repressor protein and the operator DNA sequence in the promoter of the therapeutic gene thus enabling its expression. The effective dose of tetracycline can be varied to regulate the expression of the therapeutic gene/agent and thereby optimise the effect of the therapeutic gene/agent.

The system may also be exploited to enable the regulated expression of a "suicide" gene, the expression of which in a mononuclear phagocyte would result in the death of the phagocyte carrying the gene. Selective removal of mononuclear phagocytes may then inhibit revascularisation of tumour tissue thereby restricting tumour development.

This example of regulated expression has been shown to occur in both prokaryotic (WO 9532295-A) and eukaryotic cells (28, 29) to successfully regulate the expression of both homologous and heterologous DNA sequences. This description is merely to serve as an example of how a prokaryotic sequence can be used to regulate the expression of a eukaryotic gene and is not meant to be exclusively limited to the tetracycline repressor operon.

Alternatively, or in addition, especially where internalisation of said therapeutic composition is required said therapeutic composition may further comprise an internalisation agent so as to ensure that the therapeutic composition is internalised by the mononuclear phagocytes. Agents which are suitable for ensuring internalisation of the therapeutic composition include, but are not limited to, plasminogen activation inhibitors (PAI-1 or PAI-2) or protease nexin (PN).

In yet a further preferred embodiment of the invention said binding agent is adapted to target or bind to any one or more cell surface mononuclear phagocyte molecules such as antigens or receptors. Further, said binding agent may comprise an antibody to any one or more of said molecules such as antigens or receptors, or an effective fragment of said antibody. Alternatively still said binding agent may comprise a suitable ligand either synthetically manufactured or naturally occurring.

Alternatively, the binding agent may comprise a vector. The vector may be a non-viral vector. Examples of non-viral vectors include plasmid DNA compacted with a DNA compaction agent such as one containing poly-L-lysine or a liposome or immunoliposome containing plasmid DNA compacted with a DNA-compaction agent (such as a polylysine). The non-viral vector may be a targeted non-viral vector such as plasmid DNA compacted with mannosylated PolyLysine (MPL).

In a yet further preferred embodiment of the invention said binding agent may comprise a viral vector.

The vector may be a recombinant viral vector such as an adenovirus vector, an adeno—associated viral (AAV) vector, a herpes-virus vector or a retroviral vector in which case gene delivery (transduction) is mediated by viral infection. The viral vector may be a defective viral vector which is not capable of replication in the target cells. The viral vector may also be a chimeric viral vector containing components of more than one virus such as retrovirus pseudotyped with the envelope of another virus or an adenovirus capable of expressing retroviral genetic elements (eg. Feng et al 1997 Nature Biotech. 15:866–870). Preferably the viral vector is one which is capable of preferentially transducing non-dividing cells such as a lentiviral vector, including HIV based vectors (Naldini et al 1996 Science 272: 263–267). Particularly preferred is a targeted viral vector such as a targeted adenoviral vector capable of preferentially transducing mononuclear phagocytes. Examples of methods for targeting adenoviral vectors to specific cell types are described (eg Krasnykh et al 1996 J. Virol 70: 6839–6846; Wickham et al 1996 J. Virol 70: 6831–6838); Stevenson et al 1997 J. Virol. 71: 4782–4790; Wickham et al. 1995 Gene Therapy 2: 750–756. Also preferred is a viral vector which is resistant to human complement, for example by production in a human cell line.

In any event, the viral or non-viral vector will contain a promoter to direct expression of the or each therapeutic gene and may contain additional genetic elements for the efficient or regulated expression of introduced genes, including enhancers, translation initiation signals, internal ribosome entry sites (IRES), splicing and polyadenylation signals. The enhancer may contain elements for regulated expression such as a hypoxia regulated enhancer (for example a binding element for the transcription factor HIF1) or elements which respond to stress or low glucose. The enhancer elements or elements conferring regulated expression may be present in multiple copies. Combinations of such elements are also envisaged. Genes encoding appropriate transcription factors may also be included in the vector in order to enhance the response to hypoxia, stress or low glucose. For example a gene encoding HIF1-alpha may be included in the vector (Jiang et al 1996 J Biol Chem 271: 17771–17778).

Additional vector components will be provided for other aspects of vector function such as vector maintenance, nuclear localisation, replication, and integration as appropriate using components which are well known in the art.

Suitable therapeutic genes may encode proteins which are secreted from the mononuclear phagocyte or which are retained within the cell. For treatment of cancer, suitable therapeutic genes include genes encoding proteins which act as for example: activators of anti-tumour immune mechanisms (such as cytokines, co-stimulatory molecules and immunoglobulins); of angiogenesis; or which provide enhanced drug sensitivity (such as pro-drug activation enzymes). The use of combinations of such genes is also envisaged. Genes or combinations of genes which show a by-stander effect in the destruction of neighbouring or distant tumour cells are preferred. For treatment of ischaemia, genes encoding proteins which act to stimulate angiogenesis (such as vascular endothelial growth factor (VEGF)) or other growth factors are suitable examples.

A brief list of those cell surface molecules that may be targeted by said binding agent is as follows; the receptor for human Urokinase Plasminogen Activator (uPAR; CD87); the receptor for human Colony Stimulating Factor (CSF-1); CD63; CD64; CD11b; CR3; CD33; the scavenger receptor; all or part of the receptor for the various forms of human monocyte chemoattractant protein (MCP-1, 2, etc); CD14; mannose or mannose-6-phosphate surface receptors; CD16; or HLA-DR.

In a yet further preferred embodiment of the invention said therapeutic composition comprises any one or more of the drug conjugates illustrated in Table 1, and more preferably, any combination of part I and/or part II and/or part III components specified in Table 1.

According to a yet further aspect of the invention there is provided a delivery system for targeting therapeutic compositions to hypoxic and/or ischaemic and/or stress sites comprising a hypoxia and/or ischaemia and/or stress regulatable agent and an agent for controlling the functional effectiveness thereof, and coupled thereto, a binding agent for a cell surface molecule of a mononuclear phagocyte.

According to a yet further aspect of the invention there is provided a method for targeting desired agents to hypoxic and/or ischaemic and/or stress sites comprising;
(i) coupling at least one of said agents to a binding agent that is adapted for binding or targeting a cell surface molecule expressed by a mononuclear phagocyte;
(ii) exposing said coupled agent to mononuclear phagocytes; and
(iii) allowing said mononuclear phagocytes to migrate, under conditions that support migration, either in vitro or in vivo.

According to a yet further aspect of the invention there is provided a method for treating conditions associated with hypoxic and/or ischaemic and/or stress states comprising administering to an individual to be treated the therapeutic composition of the invention.

According to a yet further aspect of the invention there is provided a method for treating conditions associated with hypoxic and/or ischaemic and/or stress states comprising withdrawing blood and/or serum from an individual to be treated and treating said blood and/or serum in vitro with a hypoxically and/or ischaemically and/or stress inducible therapeutic gene under conditions that enable incorporation of said gene into the nucleus of mononuclear phagocytes and re-injecting said treated blood and/or serum into the individual either systemically or directly into a hypoxic and/or ischaemic and/or stress area. According to a yet further aspect of the invention there is provided mononuclear phagocytes which have coupled thereto, or internalised therein, at least a hypoxia and/or ischaemia and/or stress regulatable agent and, optionally, an agent that is adapted to bind to a mononuclear phagocyte ligand which is typically found on the cell surface of said mononuclear phagocyte.

According to a yet further aspect of the invention there is provided a method for selectively destroying a mononuclear phagocyte comprising attaching thereto or internalizing therein a cytotoxic, hypoxically and/or ischaemically and/or stress activated agent and exposing said mononuclear phagocyte to hypoxic and/or ischaemic and/or stress conditions that occur either artificially by induction or occur/exist naturally.

In the instance where hypoxia and/or ischaemic and/or stress occurs/exists naturally said mononuclear phagocyte migrates in a normal manner to said hypoxic and/or ischaemic and/or stress area so that the said agent is only activated at a target area. In this way the potentially deleterious effects of mononuclear phagocytes in tumours is obviated. Moreover, having regard to the nature of said agent a bystander effect may be achieved, for example where said cytotoxic agent is released on death of said mononuclear phagocyte it may have a further deleterious effect on the hypoxic and/or ischaemic and/or stress tissue, such as, but not limited to, tumour tissue.

Many of the preferred embodiments hereinbefore described represent appropriate modifications of any one or more of the above referred to further aspects of the invention.

Embodiments of the invention will now be described by way of example only with reference to the following Figures and Table wherein:

FIG. 5A–5C. Macrophage infiltration into hypoxic areas in tumour spheroids (i.e. an in vitro model of tumour hypoxia).

Table 1 represents specific examples of drug conjugates.

Materials and Method

A preferred way of working the invention will now be described with particular reference to the use of mononuclear phagocytes to target therapeutic genes to hypoxic sites in human tumours. However, it will be understood, that this illustration of the invention ie by way of using mononuclear phagocytes to target therapeutic gene delivery is just one way in which the invention may be worked. Moreover, this example of the invention ie the targeting of therapeutic agents to human tumours is, yet again, just one example of how the invention may be worked.

EXAMPLE 1

Gene Transfer into Monocytic Cell Lines

Retroviral Transfer into the Monocytic Cell Line U937.

Techniques for retroviral vector mediated gene transfer into U937 cells (obtained from ATCC) were optimised with the marker gene β-galactosidase using retroviral particles packaged with two different envelopes. Retroviral constructs were packaged in a transient three plasmid system (Soneoka et al 1995 NAR 23 628–633); pHIT111 CMV lac Z genome with the 4070A amphotropic envelope (Soneoka et al) and the MFG CMV nuclear localisation sequence lac Z genome pseudotyped with VSV-G (Cosset et al J Virol 1995 69 7430–7436). Retroviral vectors were transduced into U937 at multiplicity of infection of 1–3 in the presence of 8 μg/ml polybrene in maintenance media (RPMI/10% FCS, obtained from Sigma) for 2 h at 37° C. Cells were stained using standard X-gal histochemical techniques 48h later (MacGregor et al 1991 p217–235, Methods in Molecular Biology, Vol 7 Ed E J Murray). Levels of transduction were approximately 0.5 % with the 4070A amphotropic envelope and approximately 1% pseudotyped with VSV-G. Transduction approaches may be increased using repeat transduction with high titre viral preparations concentrated using standard cross-flow filtration methods (following manufacturers protocol supplied by Flowgen) and co-culture with producer cell lines (Morgenstern and Land 181–206, Methods in Molecular Biology, Vol 7 Ed E J Murray). Cells transduced with pHIT111 were selected in 1 mg/ml G418 (Gibco) resulting in the isolation of stable β-galactosidase positive cell lines as determined by X gal staining. FACS based selection approaches have been established using the fluoresceinated β-galactosidase substrate FDG (fluorescein di-b-D-galactoside) according to the manufacturers protocol (Molecular Probes).

Construction of Hypoxically Regulated Retroviral Genome.

To produce a hypoxically regulatable retroviral construct long a terminal repeat (LTR) plasmid was generated from the retroviral plasmid pLNSX (Miller and Rosman 1989 Biotechniques 7 980–990) by cutting at the NheI sites within the LTR, removing the majority of the intervening retroviral genome sequences and religating the backbone. This produces an LTR plasmid in which enhancer and enhancer/promoter swaps can be engineered. The retroviral enhancer was exchanged with the PGK hypoxia response element (HRE) by performing an Nhe1/Xba1 swap. The resultant vector was then recut with Nhe1 and the Nhe 1 fragment of the retroviral genome designated MOI was inserted. MOI was generated from the MFG vector (Bandara et al 1993 PNAS 90 10764–10768) by the generation of a minimal functional packaging signal using PCR with the following primers:

HindIIIR: GCATTAAAGCTTTTGCTCT

L523: GCCTCGAGCAAAAATTCAGACGGA

The fragment generated contains MMLV nucleotides +1–+523 and thus does not contain gag coding sequences that start at +621 (numbering according to Shinnick et al 1981 Nature 293 543–548). This fragment can be isolated as a HindIII/Xho1 fragment and used to replace the corresponding region of MFG thus removing gag coding sequences. The vector also includes the SD and SA sites spanning the intron of MFG and and FMDV internal ribosome entry site (IRES) sequence to allow coincidental translation of two coding sequences from a single bicistronic mRNA. A nuclear localising lac Z (including the nls sequences from SV40 large T antigen; Bonneret 1987 PNAS 84 6795–6799) was cloned immediately 3' to this in the Stu1/Xho1 sites.

Electroporation of Monocytic Cell Lines

Electroporation conditions were optimised on the U937 and THP-1 (obtained from ATCC) monocytic cell lines using β-galactosidase and luciferase reporter constructs based on the pGL3 vector series (Promega).

Optimal conditions using the Bio Rad Gene Pulser II were determined as follows;

$1 \times 10^7$ cells were washed and resuspended in 500 µl serum free RPMI 1640 (Sigma) at room temperature then transferred to a 0.4 cm electroporation cuvette. 30 µg DNA was added and the cuvette pulsed at 300V, 950 uF giving time constants of between 20–25 milliseconds. Cells were rested at room temperature for 10 mins then seeded into 2 ml of RPMI/10% FCS (Sigma) in a 6-well plate and incubated at 37° C., 5% $CO_2$.

Transfection efficiencies were assayed by standard X-gal histochemistry (MacGregor et al 1991 p217–235, Methods in Molecular Biology, Vol 7 Ed E J Murray) and Dual reporter luciferase assay (according to manufacturers protocol obtained from Promega). Efficiencies were typically 2–5% for THP-1 and 8–14% for U937. Stable transfectants were selected either by culture in 1 mg/ml G418 (Gibco) or using FDG FACS sorting (see above).

EXAMPLE 2

Gene Transfer to Primary Human Macrophages

Primary human macrophages were isolated from leukocyte enriched blood (obtained from the Blood Transfusion Service, Southmead Rd, Bristol) as follows; peripheral blood mononuclear cells were obtained by centrifugation through a Ficoll gradient (Pharmacia) according to the manufacturer's instructions. Macrophages were obtained from this cell population by adherence on tissue culture plastic over 7 days in RPMI 1640 (Dutch modified, Sigrrma) +2% heat inactivated human AB serum (Sigma) or 10% FCS. In some experiments, isolated macrophages were subsequently cultured with the addition of 100 U/ml GM-CSF (obtained from R and D systems).

Recombinant Adenovirus Mediated Gene Transfer to Primary Human Macrophages.

Figure 4:
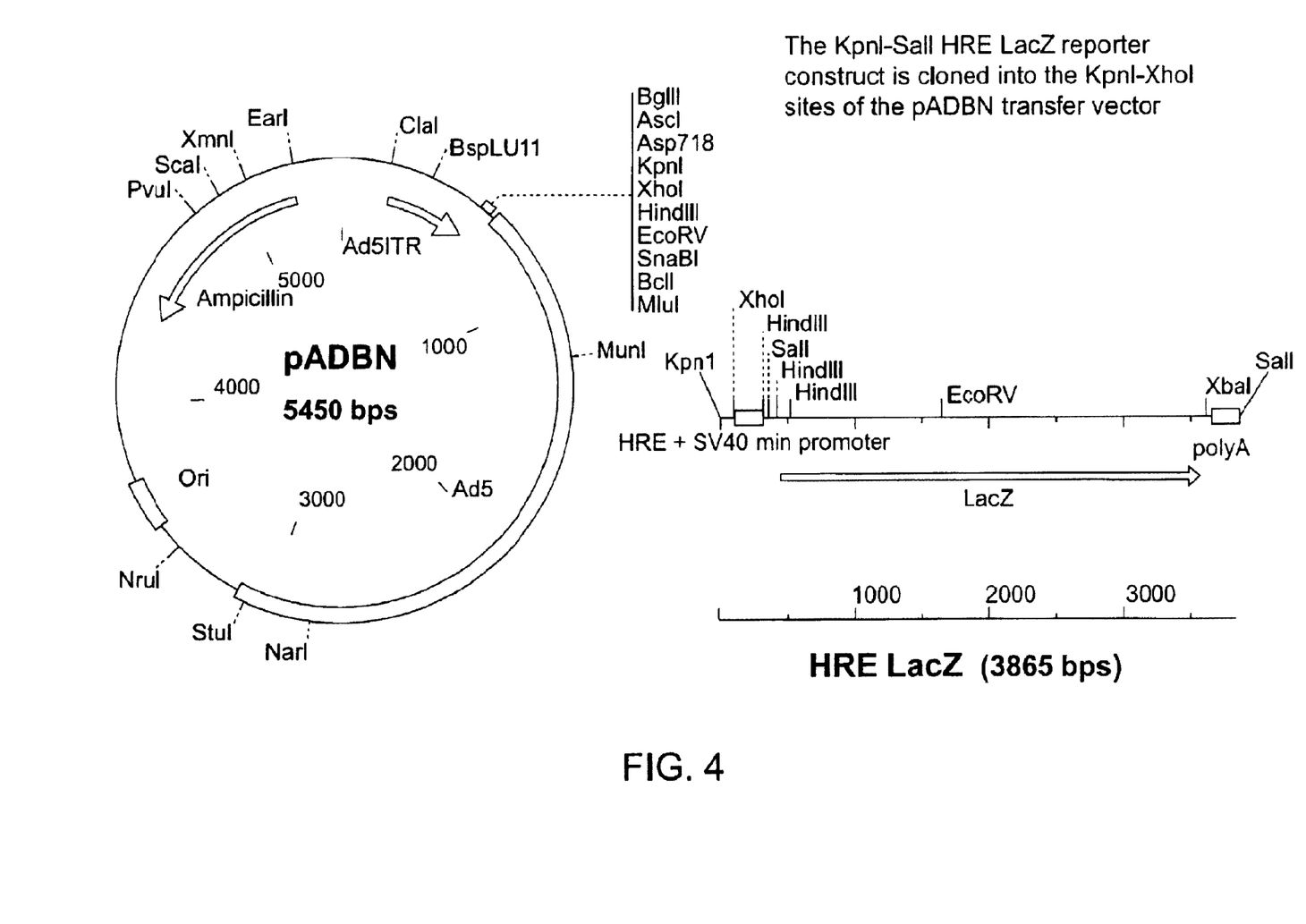
FIG. 4 shows the diagram of an Adenovirus transfer vector (QBI-HRE-LacZ) containing a LacZ gene under the control of a hypoxia regulated promoter-enhancer.
Figure 5A:
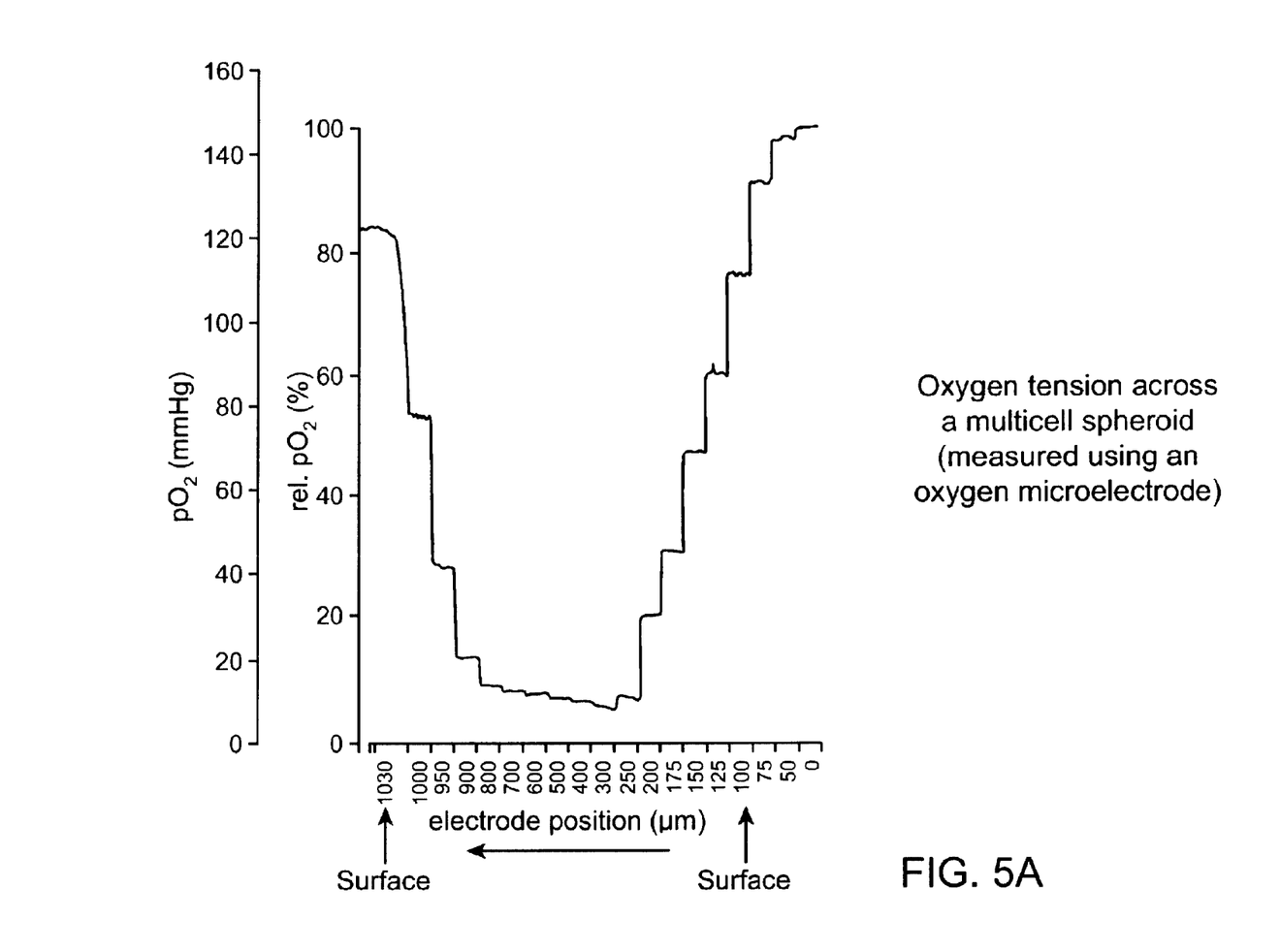
FIG. 5A shows the oxygen profile across a tumour cell spheroid. All but the cells in the outer 100 μm of these 3-D cultures are hypoxic (i.e. experiencing oxygen levels of 0–15 $pO_2$ mmHg; a level equivalent to that present in hypoxic/necrotic sites in human tumours). This hypoxia is produced by the inability of oxygen to diffuse into the central areas of spheroid. The glucose profile of the spheroid is similar to that seen for oxygen.
Figure 5B:
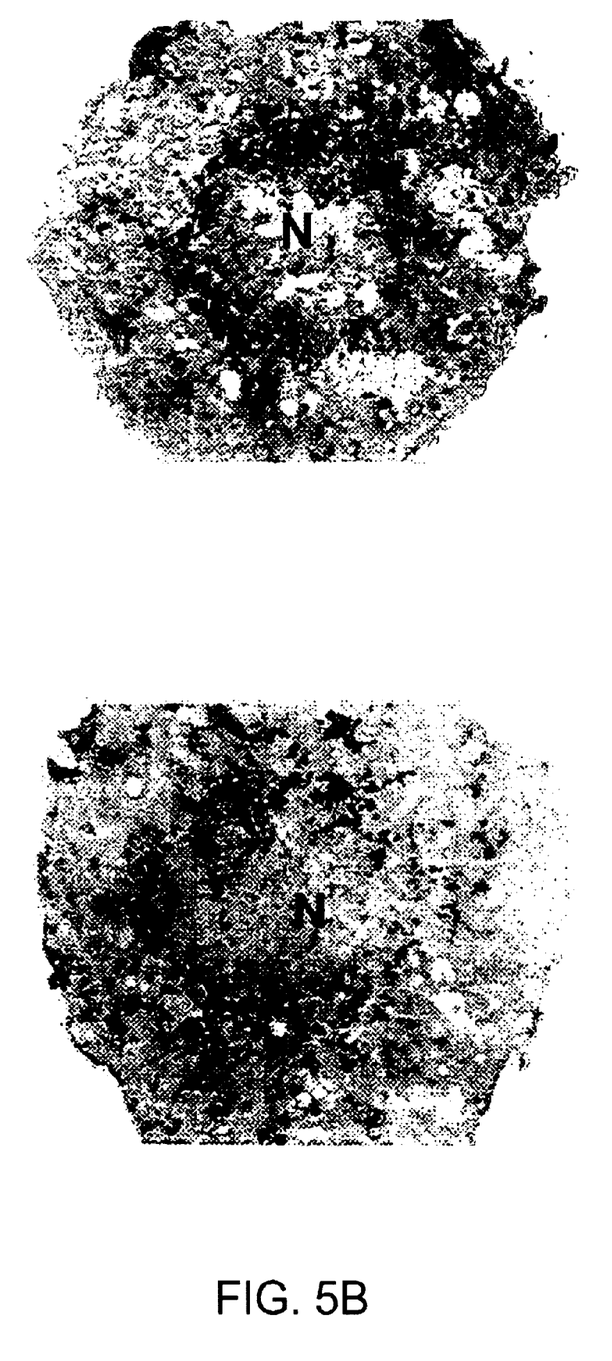
FIG. 5B shows two different tumour spheroids (made of the breast cancer cell line, MCF-7) following co-culture for 24 h with the monocytic cell line, U937. The U937 cells (darkly stained cells labelled with a monoclonal antibody to the pan-macrophage marker, CD68) accumulate in the hypoxic rim of viable, but hypoxic tumour cells around the central areas of necrosis ("N").
Figure 5C:
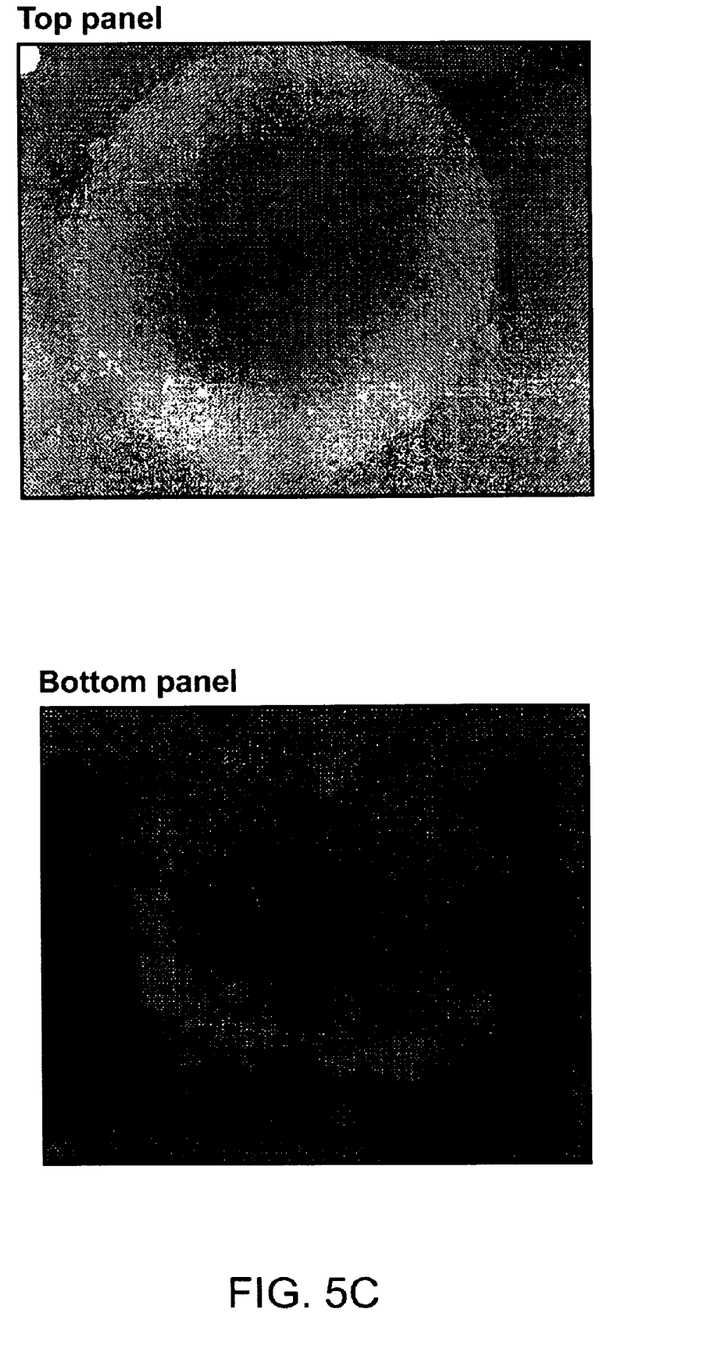
FIG. 5C shows the infiltration into tumour spheroids of U937 cells preloaded with fluorescent dye. The top panel is a light micrograph showing the opaque central area of necrosis ("N") which forms in these spheroids as a consequence of nutrient (e.g. oxygen, glucose etc) deprivation. The bottom panel is the same spheroid a fluorescent microscope to show the presence within the spheroid of the fluorescent (i.e. light coloured cells) U937 cells. The latter take up a similar position to that seen in FIG. 5B, i.e. they congregate in a collar of hypoxic tumour cells around the central areas of necrosis.

Recombinant adenoviruses were created using the Quantum Biotechnologies Adenoquest™ Kit (NBL Gene Sciences) according to the manufacturers instructions. Briefly, the cDNA/reporter construct of interest (e.g hypoxia response element nls LacZ reporter cassette) was cloned into the pADBN transfer vector (FIG. 4) The vector was linearised near the Inverted Terminal Repeat (ITR) to ensure efficient replication of the recombinant virus and was co-transfected along with the long arm of the adenoviral vector (QBI-viral DNA) into human 293 cells. Recombination in 293 cells between the homologous regions of linearised transfer vector and adenovirus genome vector produced complete adenoviral recombinants. The recombinants formed plaques in the 293 monolayer which were picked as agarose plugs, purified by plaque assay and Arklone P centrifugation and characterised by PCR (Protocols for gene transfer in neuroscience:

Towards gene therapy of neurological disorders, Chapter 8, Ed. Lowenstein & Enquist (1996) Wiley & Sons). An example of such a recombinant adenovirus is QBI-HRE-LacZ shown in FIG. 4.

Recombinant adenovirus, QBI-AdenoLacZ, containing the CMV LacZ reporter construct (4×108 PFU/ml, Quantum Biotechnologies Adenoquest™ Kit, NBL Gene Sciences) was used to infect primary macrophages seeded at a density of $7 \times 10^5$/ well in a 12 well plate. A multiplicity of infection of 80 gave an infection efficiency of 10–20% after incubation for 24 hours in the standard macrophage culture medium.

Gene Transfer to Cultured Primary Macrophages Using Mannosylated PolyLysine.

Differentiated macrophages express several cell-surface lectins/receptors including the mannose-6-phosphate receptor (Shepherd et al. 1982 J. Reticuloendothel. Soc 32: 423–431). Primary macrophages cultured for 7–14 days in the presence of GM-CSF (see above) were transfected using the pGL3 control plasmid (obtained from Promega with the luciferase coding sequence replaced by that for β-galactosidase) using mannosylated poly-L lysine:DNA complexes according to published methods (P. Erbacher et al, Human Gene Therapy 7: 721–729). This yielded 20% transfectants as determined by X-gal histochemistry (MacGregor et al 1991 p217–235, Methods in Molecular Biology, Vol 7 Ed E J Murray).

Construction of Plasmids Containing HREs

Sequences from a region approx. 300–375 bp upstream of the transcription start of the human Enolase A gene were chosen containing three HIF-1 consensus binding sites (Semenza et al 1996 J. Biol. Chem. 271: 32529–32537. The following oligonucleotides were synthesised to assemble this sequence and add a BglII site at the 5' end and a BamHI site at the 3' end.

Lead strand (75-mer)
GATCTGAGGGCCGGACGTGGGGCCCCAGAGCGACGCTGAGTGCGTG

CGGGACTCGGAGTACGTGACGGAGCC

CCG

Complementary strand (75-mer)

GATCCGGGGCTCCGTCACGTACTCCGAGTCCCGCACGCACTCAGCGT

CGCTCTGGGGCCCCACGTCCGGCCC

TCA

The oligonuclotides were inserted into the pGL3-pro vector (Promega) at the BglII site (see FIG. 7). Insertion of these oligonucleotides at this site leaves a unique BamHI site downstream of the luciferase gene for insertion of additional transcription units.For example, a transcription unit encoding HIF-1 alpha can be inserted at this site in order to further enhance the response to hypoxia.

Similarly, oligonucleotides were synthesised representing the HRE from the murine LDH gene (Firth et al 1995 J. Biol. Chem. 270: 21021–21027. The sequence chosen lies 15 bp upstream of the LDH TATAA box. It contains a HIF1 consensus binding site and a putative cyclic AMP-response element. This HRE, was also introduced at the BglII site of pGL3-pro.

Lead strand (56-mer)

GATCTCTACACGTGGGTTCCCGCACGTCCGCTGGGCTCCCACTCTGA

CGTCAGCGG

Complementary strand (56-mer)

GATCCCGCTGACGTCAGAGTGGGAGCCCAGCGGACGTGCGGGAACC

CACGTGTAGA

Cloning of the Human grp78 Promoter

The promoter was cloned by PCR amplification from human genomic DNA and includes the complete promoter/enhancer sequence and 5' UTR of the GRP78 gene Chuck et al (1992). Nucleic Acids Research. 20: 6481–64; EMBL Data Library accession no. for the GRP78 promoter sequence: X59969). The amplified fragment corresponds to bases 6–585 of this sequence. The primers used in the amplification reaction incorporated an AseI site at the 5' end and a XhoI site at the 3' end. The grp78 promoter fragment was then cloned into these sites present in a Clontech pEGFP-N1 vector allowing expression of beta-galactosidase/GFP fusion protein.

EXAMPLE 3

Infiltration of Multi-cellular Human Tumour Spheroids with Human Macrophages (U937 Cells or Monocytes)

Tumour spheroids were established in culture using the MCF-7 cell line (ATCC) using the following procedure.

A. Establishment of Spheroid Cultures

1. Uniformly sized spheroids were grown in standard 96-well tissue culture plates.
2. A 1.5% solution of agarose was prepared in media and autoclaved (the media should not contain any supplements or foetal calf serum as this causes the formation of bubbles and the cells will plate down and not form spheroids).
3. 100 μl of the agarose was aliquoted into each well and allowed to cool.
   Plates were then warmed to 37° C. before use.
4. Monolayers of tumour cell lines were stripped in the exponential growth phase, resuspended and counted using a haemocytometer. The cells were then diluted to the appropriate number of cells for spheroid initiation. For T47D and HT29 this was 1000 cells per well and for MCF-7 it was 2000 cells per well. Each well was filled with 200 μl of the cell suspension. The final concentration of the cell suspension for T47D was 5000 cells per ml. (NB spheroids were grown in the media used normally for each of the cell lines (eg T47D are grown in DMEM supplemented with antibiotics and fungicides).
5. Following initiation, the spheroids were incubated at 37° C. in a $CO_2$ incubator and left undisturbed for 5 days to allow aggregation to occur.
6. Spheroids were fed fresh medium three times per week.

B. Co-culture of Spheroids with Macrophages

1. Monocytic cell lines (eg U937 cells), peripheral blood monocytes or monocyte-derived macrophages were introduced into the spheroid culture once the spheroids have formed necrotic centres. This stage depends upon the cell line used. For MCF-7 and T47D it was after 2–3 weeks of culture, when a dark area can be seen in the centre of the spheroid.
2. This was done by removing 100 μl of media from the wells and replacing it with a suspension of macrophages (50,000 per well). For cell lines, the change in media was not a problem but for PMBC the media should be serially changed for both the spheroid and the macrophage until they are in the same media. These cells infiltrated the spheroids in the first hour of co-culture and continued to do so for up to 48 hrs. After this, the spheroids were removed from the wells using a glass Pasteur pipette, placed in a test tube and rinsed in PBS to remove any loose macrophages or cell debris.
3. The spheroids were then allowed to settle to the bottom of the tube, the PBS removed and the spheroids processed for paraffin embedding (or frozen in OCT).

Figure 3:
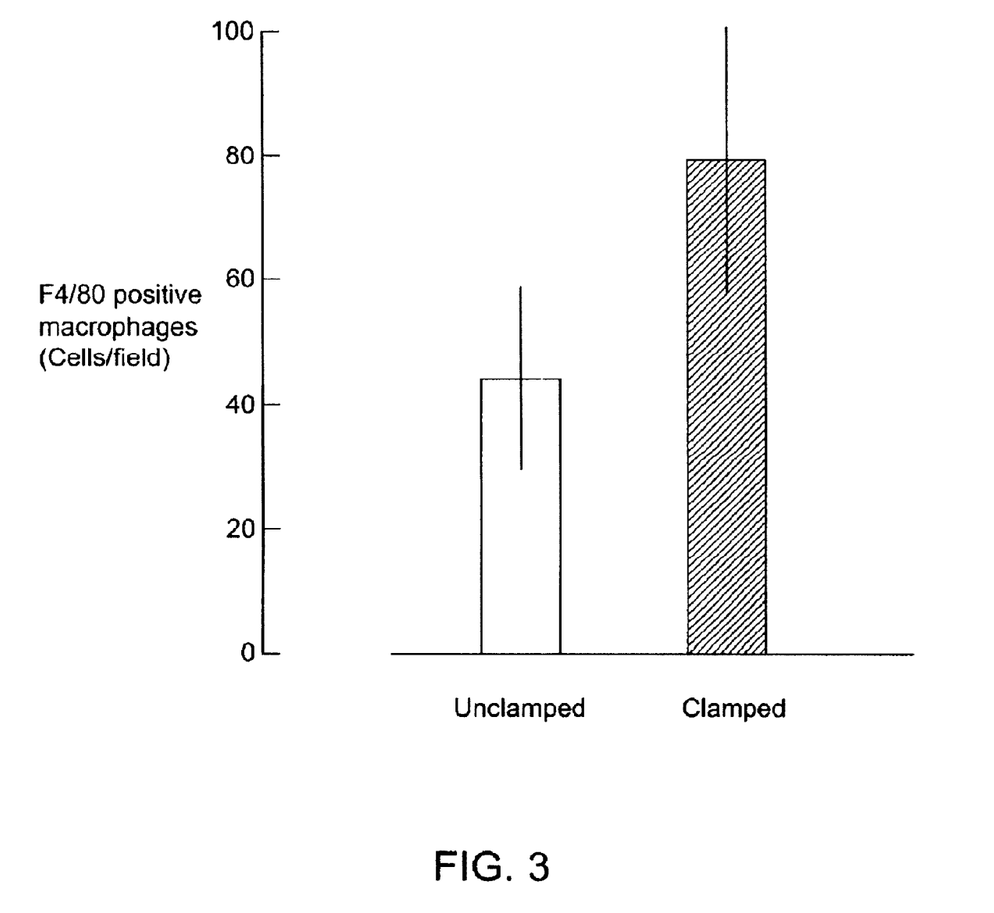
FIG. 3 shows the effect of clamp-induced hypoxia (induced by tumour vessel clamping for 2 h) on macrophage infiltration in human breast cancer xenografts grown in nude mice.

The results of an experiment showing infiltration of MCF-7 spheroids with U937 cells is shown in FIG. 3. Each spheroid displays the typical central area of necrosis ('N') surrounded by a collar of hypoxic tumour cells (approx 5–10 cells in thickness) and then several outer layers of cells that are relatively normoxic. U937 cells, immuno-labelled (dark staining) for the pan macrophage marker CD68, can be seen accumulating in the hypoxic tumour cell layers around the central necrosis.

EXAMPLE 4

Demonstration of Infiltration into Spheroids of Monocytic Cells Labelled with a Fluorescent Dye U937 cells were incubated with 90 μl of 4-(4-(didecylamino)styryl)-N-methyl pyridium iodide (2 mg/ml in abs ethanol) for 45 minutes then washed to remove the excess dye. Multicell spheroids (5–600 μm in diameter) were placed in a bacterial petri dish (agarose would fluoresce and they would adhere to tissue culture plastic) and incubated with 75000 dye-loaded U937 cells per spheroid. The final volume was 15 mls. After 4 days of co-culture, spheroids were washed to remove unattached macrophages and photographed using a fluorescence microscope.

Figure 6:
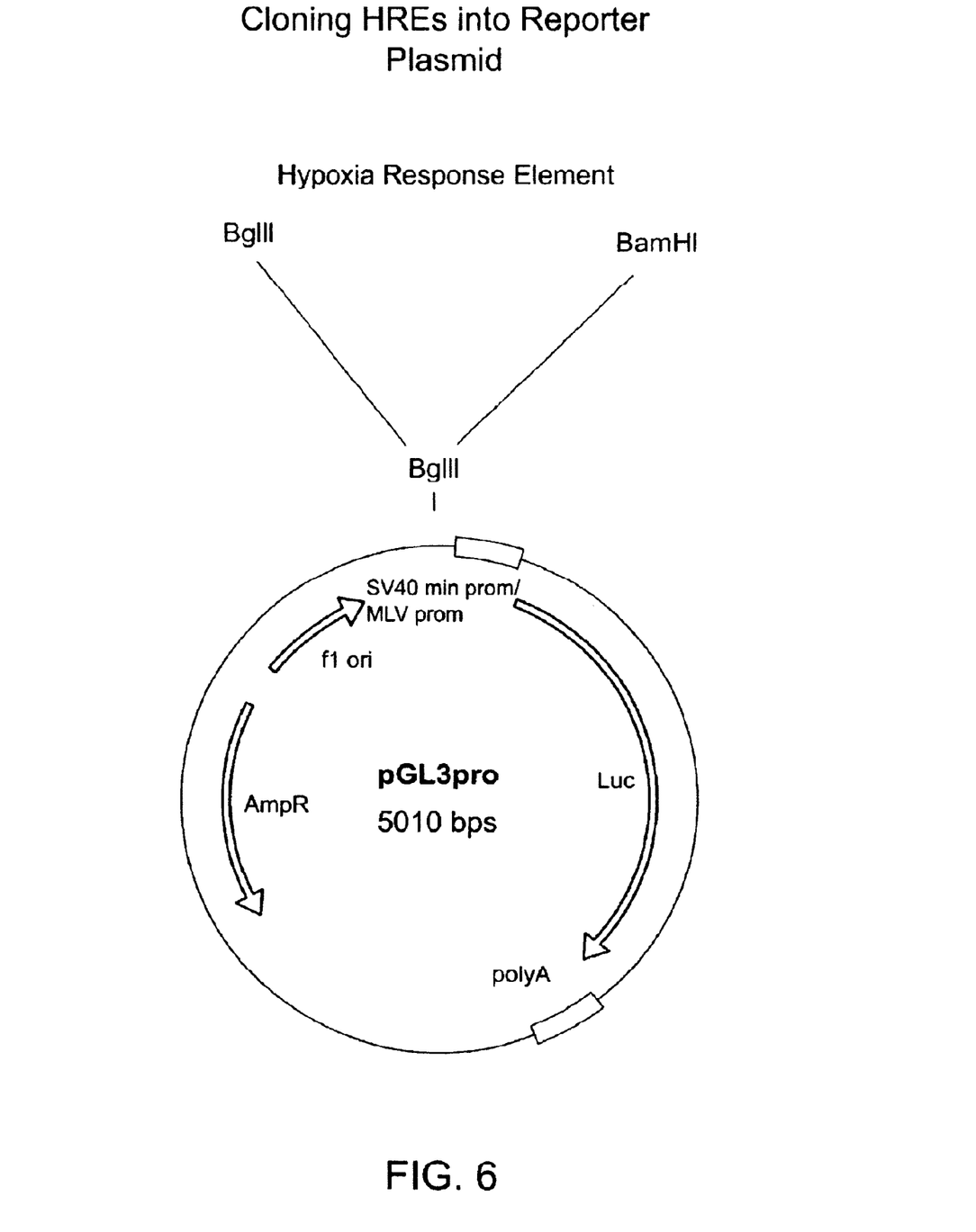
FIG. 6 illustrates cloning of HRE's in a receptor plasmid.

The result is shown in FIG. 6. Panel A in FIG. 6 shows a section through a spheroid photographed under white light. The central necrotic core (N) is visible as a dark area. Panel B, photographed under fluorescence optics, shows accumulation of macrophages labelled with fluorescent dye, in the hypoxic region around the necrotic core.

C. Paraffin embedding of spheroids

1. Spheroids were immersed in formalin for 2 hrs or overnight.
2. They were then either embedded in agar and processed or placed in a piece of pre-folded tissue paper which was then folded and placed in a tissue-processing cassette. Alternatively a Cellsafe biopsy cassette was used (a mesh chamber in which the spheroids are placed). The cassette was then closed and placed inside the processing cassette. The mesh prevented the spheroids escaping.
3. The spheroid preparations were processed through ascending grades of alcohol to paraffin wax using a Citadel 2000 Histopathology Processing Unit.
4. Sections of the paraffin wax blocks were cut using a microtome onto coated slides.

D. Immunohistochemistry for CD68 (a pan macrophage marker) to localise macrophages in spheroids 1. Spheroid sections were dewaxed in xylene and absolute alcohol.
2. The endogenous peroxidase in the sections was then blocked with 2% H202 in methanol for 10 mins.
3. Antigen retrieval: sections were exposed to proteinases type XXIV for 15 mins at 37° C.
   The sections were then incubated in the following: (with 3×5 min washes between each step)
4. Normal serum for 30 mins at room temperature
5. Primary anti-CD68 monoclonal antisera at a dilution of 1:100 for 1 hr at room temperature or overnight at 40° C.
6. Secondary antibody (biotinylated horse anti-mouse IgG) for 30 mins at room temperature followed by an avidin-biotin-peroxidase complex for 30 minutes at room temperature (ie using the Vector ABC Elite kit)
7. Visualized with the chrornagen, DAB or AEC for 20 10 mins.

8. The nuclei were then counterstained with haematoxylin and sections mounted with coverslips for viewing.

NB Spheroid sections needed to be washed thoroughly in diluent between each step of the staining protocol to limit background/non-specific staning.

EXAMPLE 5

Effect of Clamp-induced Hypoxia on Macrophage Infiltration into Tumour Xenografts In order to determine the effect of hypoxia on macrophage infiltration into tumours in vivo, a xenograft model was established in which a human breast-tumour derived cell line is grown under the skin in nude mice. Clamping of the tumours induces increased hypoxia in the tumours.

A. Implantation and clamping of breast tumour xenografts in nude mice
   (as described in Griffiths L et al 1997 Cancer Res 57: 570–72)
   1. Male nu/nu mice were injected s.c. with 5×107 MDA-231 cells in the dorsal area in a volume of 0.1 ml. Twelve animals were used per experimental group.
   2. When the tumours reached 600 mm$^3$ (ie after 6–7 weeks of growth) they were clamped for 2 h to occlude the blood supply and induce radiobiological hypoxia (<1% oxygen). Control tumours were not clamped. (NB this procedure only partially occludes the blood supply to the tumour, thereby allowing continued macrophage infiltration into the tumour).
   3. Tumours were excised immediately following clamp removal, fixed and paraffin-embedded for routine histology and/or immunohistochemistry for the pan murine macrophage marker, F4/80.

B. Immunohistochemistry for the pan murine macrophage marker. F4/80
   1. Sections were dewaxed and rehydrated through graded alcohols to distilled water.
   2. Antigen retrieval: Serotec's reagent, STUF, was used to unmask antigen (as described by the manufacturers).
   3. Slides were then washed in PBS/0.1% Trition-X-100: 3 changes×5 mins each.
   4. Endogenous peroxidase was blocked in sections in 2% $H_2O_2$/methanol for 20 mins.
   5. Sections were then washed as in Step 3.
   6. Non specific protein binding sites in sections were blocked using 5% normal rabbit serum in PBS for 30 mins.
   7. Sections were then incubated in Serotec's F4/80 diluted to 1:20 in normal rabbit serum (5% NRS in PBS) for 90 mins at RT.
   8. Sections were then washed as in Step 3.
   9. The Vector biotinylated rabbit anti-rat (mouse absorbed) at 1:100 in PBS was then placed on the sections for 45 mins at RT.
   10. Sections were then washed as in Step 3.
   11. Sections were then incubated in Vector ABC reagent for 45 mins at RT.
   12. Sections were then washed in Step 3.
   13. The brown colour reaction was then developed with Vector DAB kit for 2 mins.
   14. The sections were then washed in water and nuclei was counterstained in haematoxylin.
   15. After dehydrating through alcohols, cleared in Xylene and mounted with coverslips, the number of F4/80 positive macrophages was then estimated for each tumour by taking the average of the counts from 20, randomly selected fields of view (×20 objective) obtained using a SeeScan image analysing device.

The results of this experiment are shown in FIG. 3. Clamping of the tumours led to increased infiltration of macrophages, demonstrating a correlation between the degree of hypoxia and the number of infiltrating macrophages.

Further Examples of Therapeutic Compositions For use in Working the Invention

Table 1 represents examples of drug conjugates for attaching to, or internalising in, mononuclear phagocytes.

The drug conjugate of choice can be infused (repeatedly or as a single injection) into the general circulation so as to bind in vivo to the surface of systemic mononuclear phagocytes and/or macrophages already resident in diseased tissues (e.g. malignant tumours). In support of the aforementioned mode of drug delivery is the finding that when a monoclonal antibody, specific for the Mac-1 antigen on macrophages, is conjugated to indium (a radioactive element) and injected intravenously into mice bearing a solid tumour, it was seen on scintographs to accumulate predominantly in the cancer lesion (9). Alternatively the drug conjugate can be exposed to monocytes ex vivo, following their purification from the blood of patients using such standard methods as Ficoll-Hypaque gradients and elutriation as described previously in (10).

Homing of blood monocytes loaded up with drug conjugates into malignant tumours can be augmented by prior treatment with conventional systemic therapies which induce local inflammation/necrosis in the diseased tissue (e.g. radiotherapy or chemotherapy in the case of cancer patients). This stimulates the release of chemoattractant factors for monocytes/macrophages such as MCP-b 1(11, 12) and would thus enhance the delivery and hence the therapeutic efficacy of the drug conjugate at the diseased site.

Mode of production of selected drug conjugates

Drug 1. (with reference to Table 1) RSU1069-F(ab)$_2$ of a monoclonal antibody to CD87 (uPAR)

This conjugate uses a highly specific F(ab)$_2$ fragment a monoclonal antibody to CD87 (urokinase plasminogen activator receptor; uPAR) to target naturally occurring uPAR on the surface of monocytes and macrophages.

A monoclonal antibody to CD87 is made as described in (13) and then cleaved/purified to a specific F(ab)$_2$ monoclonal antibody fragment using standard proteolytic methods. Depending upon the part of uPAR used to raise the antibody (i.e. as the antigen), the epitope for the antibody generated may either be in the (i) ligand (i.e. uPA)-binding portion of the uPAR (in which case the drug conjugate will only bind to unoccupied uPAR on monocytes/macrophages), or (ii) the non ligand (i.e. uPA)-binding portion of the uPAR (in which case the drug conjugate will bind to both unoccupied and unoccupied UPAR on monocytes/macrophages). The most effective drug uptake is likely to be achieved using the latter form of conjugate.

The fragment of the CD87 monoclonal antibody is conjugated to the bioreductive prodrug, RSU1069, by the latter being reacted with an agent such as arylazide to add a N-hydroxysuccinimide group. This is then cross-linked at neutral pH to the CD87 antibody fragment via amine groups to form a conjugate. This method is well established for conjugating drugs to proteins and is described fully in (14).

Drug 2. (with reference to Table 1) i.e. RSU1069-PAI-2

This conjugate uses the affinity of plasminogen activator inhibitor 2 (PAI-2) for urokinase plasminogen activator receptor (uPAR)—urokinase plasminogen activator complexes to target the bioreductive prodrug to the surface of monocytes and macrophages. PAI-2 triggers the internalization of uPAR-uPA complexes, so the internalization by these cells of the bioreductive prodrug attached to PAI-2 is assured.

Naturally occurring PAI-2 is obtained from the culture supernatant of human blood monocytes stimulated maximally with interleukin 1 or 2 as described in (15). This is then purified to homogeneity in the usual manner by elution from an anti-PAI-2 immunoaffinity column. Alternatively, PAI-2 can be produced in a recombinant expression system and purified according to the method of (16). The PAI-2 preparation is then conjugated to RSU1069 using the method outlined as hereinbefore described for drug 1(14).

Drug 6. (with reference to Table 1) i.e. Interleukin-2 (IL-2) gene linked to hypoxia responsive promoter.

This gene is transferred to monocytes/macrophages using a replication-defective adenoviral vector. Efficient transfer of genes into human macrophages has been achieved with this method with expression of the gene in 40–80% of the cells exposed to the vector and lasting up to 3 weeks after gene transfer (10).

Defective retroviral vectors, direct DNA internalization or such non-gene viral gene transfer systems can also be used such as cationic lipids, liposomes, lectins or polymers. Genes other than IL-2 which could be of therapeutic benefit include such other immunomodlators as TNFá, or interferon gamma, prodrug activating enzymes, enzyme inhibitors, tumour antigens (to provoke the hosts immune reactivity to the tumour) and anti-oncogenes (antibodies or antisense RNA). It will be understood by those skilled in the art that the DNA construct used may, embody a number of these genes rather than just one and is not intended to limit the scope of the application.

The hypoxically inducible expression control sequence (promoter) for the Epo or PGK genes (or multiple copies thereof) is/are coupled to one or more of the gene sequences of choice (e.g. IL-2 gene sequence) as described by one of us previously in (17).

Ex vivo gene transfer:

The method outlined in (10) involves incubating (under sterile conditions) freshly isolated blood monocytes or monocyte-derived macrophages (monocytes incubated overnight in teflon bags or on plastic cultured wells) in the presence of 100 plaque-forming units per cell of the purified replication-defective vector, Ad.RSVá, harbouring the hypoxia-responsive promoter-Il-2 gene construct in RPM1 incubation medium (1 ml/$10^6$ cells). Gene transfer may be enhanced by simultaneous treatment of the cells with 10 U/ml of human interferon gamma. Cells are then washed to remove free viral particles and interferon gamma and reincubated at 37° C. in fresh RPMI medium in teflon bags. The same adenoviral vector but harbouring the *E.coli* â-galactosidase gene (Ad.RSV.âgal) instead of the hypoxia-responsive promoter-IL-2 gene construct is used as a reporter gene (i.e. to check the efficiency of this gene transfer method to monocytes/macrophages ex vivo). The presence of the â-gal enzyme in cells after infection with Ad.RSV.âgal is then assessed using histochemical methods as described in (17). The transfected cells ($10^8$ to $10^9$ cells) are then injected sterile back into the bloodstream or directly into the appropriate diseased tissue (e.g. malignant tumour) of the donor as in (10).

In vivo gene transfer:

This is performed according to the in vivo method of adenoviral gene delivery described in (18). This involves injecting the vector (i.e. Ad.RSVâ) bearing the hypoxia-responsive promoter-IL-2 gene construct into the bloodstream (primarily to label monocytes) and/or into the diseased tissue (at $10^9$ to $10^7$ plaque-forming units) to label tissue macrophages.

The invention is exemplified by the drug conjugate candidates in Table 1. It will be understood by those skilled in the art that such conjugates represent selected examples and are not intended to limit the scope of the invention, furthermore it will be understood that indeed any one example of a candidate Part I drug conjugate may, where appropriate, be used in conjunction with any one example of a Part II candidate and/or any example of a Part III candidate. Additionally it will be understood that any example of a Part III candidate may be used in conjunction with any example of a Part II and/or Part I candidate drug conjugate.

The invention hereinbefore described therefore represents a most elegant and effective means and method of delivering a therapeutic and/or cytotoxic agent to a hypoxic or ischaemic or stress site by use of monocytes and/or macrophones and their natural ability to congregate at a hypoxic site.

TABLE 1

SPECIFIC EXAMPLES OF DRUG CONJUGATES

| | Part 1 | Part II | Part III |
|---|---|---|---|
| Drug 1 | RSU1069 or Tirapazamine | F(ab)2 to CD87 (uPAR) | — |
| Drug 2 | RSU1069 or Tirapazamine | PAI-2 (binds to receptor bound urokinase plasminogen activator (uPAR) & ensures internalization of drug) | — |
| Drug 3 | RSU1069 or Tirapazamine | PAI-2 (binds to receptor bound uPAR & ensures internalization of drug) | NADPH:P450 reductase (reductase for activation of RSU1069 or Tirapazamine under hypoxia) |
| Drug 4 | RSU1069 or Tirapazamine | F(ab)2 to CSF-1 receptor (binds to human CSF receptor on surface of monocyte/macrophages) | NADP:P450 reductase |
| Drug 5 | Cytosine deaminase (prodrug activating enzyme) | F(ab)2 to CD63 | — |
| Drug 6 | Gene for Interleukin 2 (immuno-stimulatory cytokine) in Ad.RSV | | Hypoxia. or ischaemia or stress -resp. promoter sequence |
| Drug 7 | DNA sequence for soluble domain of VEGF receptor (eg. flk-1) in Ad. RSV | — | Hypoxia. or ischaemia or stress -resp. promoter sequence |

TABLE 1-continued

SPECIFIC EXAMPLES OF DRUG CONJUGATES

| | Part 1 | Part II | Part III |
|---|---|---|---|
| Drug 8 | A therapeutic gene for example as described in PCT/GB95/00322 W09521927 | pGL3-pro plasmid and mannosylated poly-L lysine | Hypoxia or ischaemia or stress -resp. promoter sequence |
| Drug 9 | A therapeutic gene for example as described in PCT/GB95/00322 WO9521927 | Adenoviral vector for example QBI-HRE-LacZ | Hypoxia or ischaemia or stress -resp. promoter sequence |

REFERENCES

1. O'Sullivan C and Lewis C E (1994) J. Pathol. 172: 229–235.
2. Leek R D, Lewis C E, Whitehouse R and Harris A L. (1996) Cancer Research 56:4625–4629.
3. Knighton D R, et al. (1983) Science. 221: 1238–85
4. Vaickus L and Foon K A. (1991). Cancer Invest. 9:195–209.
5. Byers V S and Baldwin R W. (1988). *Immunol.* 65: 329–409
6. Sands H. (1988). *Antibody Immunoconjug. Radiopharm* 1:213–226.31.
7. Epenetos A A. et al. (1986). *Cancer Res.* 46:3183–91.
8. Derbyshire E J and Thorpe P E. (1996). In *"Tumour Angiogenesis"* Eds R. Bicknell, C E Lewis & N. Ferrara. Oxford University Press, Oxford. (in press).
9. Collette B. et al. (1988). *Cancer Immunol. Immuno. Ther.* 26: 237–242.
10. Haddada H., et al. (1993). *Biochem. Biophys. Res. Commun.* 195: 1174–83.
11. Mantovani A., et al. (1993). *Res. Immunol.* 144: 280–83.
12. Martinet N., et al. (1992). *Cancer.* 70: 854–60.
13. Ronne E., et al. (1991). *FEBS Letts.* 288: 233–36.
14. Gabor F., et al. (1995). *Archiv. der Pharmazie.* 328: 775–80.
15. Gyetko M. R., et al. (1993). *J Leuk. Biol.* 53: 598–601.
16. Steven F., et al. (1991). *Eur. J Biochem* 196: 431–8.
17. Ratcliffe P. J., Firth J. D., and Harris A. L. (1994). Patent application entitled "Targeting gene therapy". PCTIGB95/00322.
18. Magovern C. J., et al. *Ann. Thorac. Surg.* 62: 425–33.
19. Attenello J. W., Lee A. S., (1984). *Science* 226:187–1909.
20. Gazit G., Kane S. E., Nichols P., Lee A. S., (1995). *Cancer Res.* 55: 1660–63.
21. Valdivia R. H., Falkow S., (1996). *Molecular Microbiology* 22: 367–78.
22. Brown L. F., Papadopoulossergiou A., Berse B., Manseau E. J., Tognazzi K., Perruzzi C. A., Dvorak H. F., Senger D. R., (1994). *AM. J. Pathol.* 145: 610–623.
23. Hijiya N., Setoguchi M., Matsura K., Higuchi Y., Akizuki S., Yamamoto S., (1994). *Biochem. J.* 303: 255–262.
24. Takahashi Y., Bucana C. D., Liu W. B., Yoneda J., Kitadi Y., Cleary K. R., Ellis L. M., (1996). *J. Natl. Canc. Inst.* 88: 1146–1151.
25. Griffiths L., Dachs G U., Bicknell R., Harris A. L., & Stratford I., (1997). *Cancer Res.* 57 (in press; Feb. issue).
26. Savill J. (1996). *Biochem. Soc. Trans.* 24: 1065–69.
27. Sugawara S., Takeda K., Lee A., Dennert G., (1993). *Cancer Res.* 53: 6001–5005.
28. Wirtz E and Clayton C. (1995). Science 268: 1179–1183.
29. Schmid S. L. (1995). Trends in Cell Biology 5: 267–268.
30. Chen L. et al (1996) Cancer Research 56:1331–1340.
31. Negus R. P., Stamp G. W., Hadley J., Balkwill K., (1997) Am. J. Pathol. 150:1723–1734.

What is claimed is:

1. A mononuclear phagocyte modified to comprise at least one regulatable element operably linked to at least one nucleotide sequence of interest (NOI), wherein said regulatable element is capable of regulating expression of said NOI in a tumour site and is selected from a hypoxia regulatable element, an ischemic regulatable element and a stress regulatable element.

2. The mononuclear phagocyte according to claim 1 wherein the mononuclear phagocyte comprises a binding agent capable of binding to a cell surface element of the mononuclear phagocyte.

3. The mononuclear phagocyte according to claim 2 wherein the binding agent comprises a mannosylated poly-L-lysine ligand.

4. The mononuclear phagocyte according to claim 2 wherein the binding agent comprises a viral vector for internalising the regulatable element into the mononuclear phagocyte.

5. The mononuclear phagocyte according to claim 1 wherein the NOI is incorporated into the genome of the mononuclear phagocyte.

6. The mononuclear phagocyte according to claim 4 wherein the viral vector is a lentiviral vector.

7. The mononuclear phagocyte according to claim 1 wherein the mononuclear phagocyte further comprises an NOI encoding HIF1-alpha or a tetracycline repressor protein.

8. The mononuclear phagocyte according to claim 1 wherein the at least one NOI encodes a pro-drug activation enzyme.

9. A construct comprising at least one regulatable element operably linked to at least one nucleotide sequence of interest (NOI), wherein said regulatable element is selected from a hypoxia regulatable element, an ischemic regulatable element and a stress regulatable element, and wherein the construct is coupled to a binding agent tat is capable of selective binding to a cell surface element of a mononuclear phagocyte.

10. The construct according to claim 9 wherein the regulatable element is an HRE element.

11. The construct according to claim 9 or claim 10 wherein the binding agent comprises a ligand adapted to bind to the cell surface element.

12. The construct according to claim 9 or claim 10 wherein the binding agent comprises a viral vector for internalising the regulatable element into a mononuclear phagocyte.

13. The construct according to claim 12 wherein the viral vector is selected from the group consisting of an adenoviral vector and a lentiviral vector.

14. A method for internalising a regulatable element into a mononuclear phagocyte wherein the regulatable element is selected from a hypoxia regulatable element, an ischemic regulatable element and a stress regulatable element and the method comprises:

providing a mononuclear phagocyte ex vivo; and
exposing the mononuclear phagocyte to a construct as defined in any one of claims 9 or 10 under conditions sufficient to internalise the construct into the mononuclear phagocyte.

15. A composition comprising a mononuclear phagocyte according to claim 1 optionally admixed with a pharmaceutically acceptable diluent, excipient or carrier.

16. A composition comprising a construct according to claim 9 optionally admixed with a pharmaceutically acceptable diluent, excipient or carrier.

17. A mononuclear phagocyte comprising an NOI encoding a p450 enzyme wherein the NOI has been internalised into the mononuclear phagocyte by an adenoviral vector; and wherein the NOI encoding the p450 enzyme is operably linked to a hypoxia response element (HRE); such that the p450 enzyme is expressed under suitable hypoxic conditions.

18. The mononuclear phagocyte according to claim 8 wherein the pro-drug activation enzyme is a p450 enzyme.

19. The mononuclear phagocyte according to claim 18 wherein the p450 enzyme, is a CYP2B6 p450 enzyme.

20. The construct according to claim 11 wherein the ligand is a mannosylated poly-L-lysine.

* * * * *